US012588894B2

(12) United States Patent
Sudol

(10) Patent No.: US 12,588,894 B2
(45) Date of Patent: Mar. 31, 2026

(54) IMAGING ASSEMBLY FOR INTRALUMINAL IMAGING

(71) Applicant: KONINKLIJKE PHILIPS N.V., Eindhoven (NL)

(72) Inventor: Wojtek Sudol, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 773 days.

(21) Appl. No.: 16/491,110

(22) PCT Filed: Mar. 7, 2018

(86) PCT No.: PCT/EP2018/055576
§ 371 (c)(1),
(2) Date: Sep. 4, 2019

(87) PCT Pub. No.: WO2018/162536
PCT Pub. Date: Sep. 13, 2018

(65) Prior Publication Data
US 2020/0008780 A1 Jan. 9, 2020

Related U.S. Application Data

(60) Provisional application No. 62/468,138, filed on Mar. 7, 2017.

(51) Int. Cl.
*A61B 8/00* (2006.01)
*A61B 8/12* (2006.01)
(Continued)

(52) U.S. Cl.
CPC ............... *A61B 8/445* (2013.01); *A61B 8/12* (2013.01); *A61B 8/4272* (2013.01);
(Continued)

(58) Field of Classification Search
CPC ......... A61B 8/445; A61B 8/12; A61B 8/0891; A61B 8/00
See application file for complete search history.

(56) References Cited

U.S. PATENT DOCUMENTS 5,924,997 A * 7/1999 Campbell ............ A61B 8/4461
600/549
5,947,905 A 9/1999 Hadjicostis
(Continued)

FOREIGN PATENT DOCUMENTS

EP 0853919 A2 7/1998
WO WO-2004034694 A2 * 4/2004 ........... A61B 8/0841
(Continued)

OTHER PUBLICATIONS

International Search report and written opinion of PCT/EP2018/055576 dated Aug. 10, 2018.

*Primary Examiner* — Pascal M Bui Pho
*Assistant Examiner* — Michael Yiming Fang

(57) ABSTRACT

An intraluminal imaging device is provided. In one embodiment, the imaging device includes a flexible elongate member that may to be inserted into a body lumen within a patient. The flexible elongate member has a central longitudinal axis. The imaging device also has an imaging assembly that is disposed at a distal portion of the flexible elongate member. The imaging assembly comprises a flexible substrate and a plurality of ultrasound transducer elements. The plurality of ultrasound transducer elements are disposed on the flexible substrate. The flexible substrate is disposed around the central longitudinal axis of the flexible elongate member such that the ultrasound transducer elements are oriented to face away from the central longitudinal axis and the flexible substrate.

21 Claims, 6 Drawing Sheets

(51) Int. Cl.
    *B06B 1/06*         (2006.01)
    *A61B 8/08*         (2006.01)

(52) U.S. Cl.
    CPC .......... *A61B 8/4494* (2013.01); *B06B 1/0625*
        (2013.01); *A61B 8/0891* (2013.01); *A61B*
        *8/4488* (2013.01); *B06B 2201/76* (2013.01)

(56)           References Cited

U.S. PATENT DOCUMENTS

| | | | |
|---|---|---|---|
| 7,226,417 B1 | 6/2007 | Eberle | |
| 9,070,865 B1 | 6/2015 | Snook | |
| 2002/0087083 A1* | 7/2002 | Nix | A61B 8/12 |
| | | | 600/459 |
| 2006/0074317 A1 | 4/2006 | Satou | |
| 2006/0103265 A1 | 5/2006 | Miyoshi | |

| | | | |
|---|---|---|---|
| 2007/0239024 A1 | 10/2007 | Eberle | |
| 2008/0154136 A1* | 6/2008 | Webler | A61B 90/36 |
| | | | 600/463 |
| 2008/0200811 A1 | 8/2008 | Wakabayashi | |
| 2010/0262014 A1 | 10/2010 | Huang | |
| 2013/0018269 A1 | 1/2013 | Matsumoto | |
| 2014/0187960 A1* | 7/2014 | Corl | A61B 8/4483 |
| | | | 600/466 |
| 2015/0282783 A1* | 10/2015 | Katsura | B06B 1/0629 |
| | | | 600/462 |
| 2015/0305710 A1* | 10/2015 | Stigall | A61B 8/0891 |
| | | | 600/424 |
| 2017/0303893 A1* | 10/2017 | Sato | A61B 8/445 |

FOREIGN PATENT DOCUMENTS

| | | | | |
|---|---|---|---|---|
| WO | WO-2017014749 A1 * | 1/2017 | ............ | A61B 8/445 |
| WO | 2017167889 A1 | 10/2017 | | |

* cited by examiner

500

Form a plurality of ultrasound transducer elements on a flexible substrate — 502

Position the imaging assembly at a distal portion of a flexible elongate member — 504

Arrange the plurality of ultrasound transducer elements in an annular configuration — 506

Orient the ultrasound transducer elements to face away from the central longitudinal axis — 508

IMAGING ASSEMBLY FOR INTRALUMINAL IMAGING

RELATED APPLICATION

The present disclosure claims the benefit of and priority to U.S. Provisional Application No. 62/468,138, filed Mar. 7, 2017, which is incorporated by reference in its entirety.

TECHNICAL FIELD

The present disclosure relates generally to array-based intraluminal imaging, such as phased array intravascular ultrasound (IVUS) imaging. In particular, an array assembly on a flexible substrate of an intraluminal imaging catheter is described.

BACKGROUND

Intravascular imaging is widely used in interventional cardiology as a diagnostic tool for assessing a diseased vessel, such as an artery within the human body, to determine the need for treatment. Intravascular imaging can further be used to guide the intervention and/or to assess the effectiveness of the intervention. An intravascular imaging device including one or more ultrasound transducers is passed into the vessel and is guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an intravascular imaging system. The imaging system processes the received ultrasound echoes to produce a cross-sectional image of the vessel where the device is placed.

Solid-state (also known as synthetic-aperture) intravascular imaging catheters are one of the two types of intravascular imaging devices commonly used today, the other type being the rotational intravascular imaging catheter. Solid-state intravascular imaging catheters carry an imaging device that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state intravascular imaging system can synthesize the effect of a mechanically scanned ultrasound transducer but without moving parts (hence the solid-state designation). Since there is no rotating mechanical element, the transducer array can be placed in direct contact with the blood and close to the vessel tissue with minimal risk of vessel trauma. Furthermore, because there is no rotating element, the electrical interface is simplified. The solid-state scanner can be wired directly to the imaging system with a simple electrical cable and a detachable electrical connector, unlike the complex rotating electrical interface used for a rotational intravascular imaging device.

Efficiently manufacturing an ultrasound imaging device with good acoustic performance and image quality is challenging. The imaging assemblies of some existing devices include a flexible substrate that is manufactured of a material having an unsuitable acoustic impedance for high image quality. Additionally, since the transducer array can be placed in direct contact with the body tissue or body fluid including the blood, it is important that the intraluminal imaging devices are completely sealed. For example, an additional step may be required to join and seal two edges of a flexible substrate in current devices.

SUMMARY

Embodiments of the present disclosure provide an improved intraluminal imaging system for generating images of a lumen within the body of a patient, such as a blood vessel. An ultrasound imaging assembly includes a flexible substrate on which transducer elements are formed. The flexible substrate is positioned around a central longitudinal axis of a flexible elongate member such that the transducer elements face outwardly away from the central longitudinal axis. One or more acoustic matching layer(s) are positioned around the transducer elements. The acoustic matching layer(s) enhance the transmission of ultrasound energy outwardly away from the central longitudinal axis and into the body tissue. The acoustic matching layers(s) also provide a continuous seal around the imaging assembly that prevent fluid ingress.

In some embodiments, an intraluminal imaging device is provided. The intraluminal imaging device includes a flexible elongate member that may be inserted into a body lumen within a patient. The flexible elongate member may comprise a central longitudinal axis. The intraluminal imaging device may also include an imaging assembly that is disposed at a distal portion of the flexible elongate member. The imaging assembly may include a flexible substrate and a plurality of ultrasound transducer elements. The plurality of ultrasound transducer elements may be disposed on the flexible substrate. The flexible substrate may be disposed around the central longitudinal axis of the flexible elongate member such that the ultrasound transducer elements are oriented to face away from the central longitudinal axis and the flexible substrate.

In some embodiments, the imaging assembly may further comprise a support member such that the flexible substrate is positioned around the support member. In some embodiments, the imaging assembly also comprise a backing material that may be disposed between the flexible substrate and the support member. In some examples, the support member may define a lumen to accommodate a guide wire extending along the central longitudinal axis.

In some embodiments, the imaging assembly may further comprise an outer shell positioned around the flexible substrate such that the plurality of ultrasound transducer elements contact the outer shell. In some embodiments, the imaging assembly may further comprise a filling material positioned in a space between adjacent ultrasound transducer elements, the flexible substrate, and the outer shell. In some examples, the outer shell may comprise an acoustic matching layer. In some examples, the outer shell may comprise of two or more acoustic matching layers. In some other examples, the outer shell may seal the imaging assembly to prevent fluid ingress.

In some embodiments, a method of assembling an intraluminal imaging device is provided. The method includes positioning an imaging assembly at a distal portion of a flexible elongate member that may be inserted into a body lumen within a patient. The imaging assembly may comprise a plurality of ultrasound transducer elements that are formed on a flexible substrate. The method also includes arranging the plurality of ultrasound transducer elements around a central longitudinal axis of the flexible elongate member. The method further includes orienting the ultrasound transducer elements to face away from the central longitudinal axis and the flexible substrate.

In some embodiments, the method of assembling the intraluminal imaging device may include positioning the flexible substrate around a support member and inserting a backing material between the flexible substrate and the support member. In some examples, the support member may have a cylindrical shape. In some examples, positioning the imaging assembly may include arranging the support member along the central longitudinal axis of the flexible elongate member. In some embodiments, the method of assembling the intraluminal imaging device may further include extending a guide wire along the central longitudinal axis of the flexible elongate member within a lumen defined by the support member.

In some embodiments, the method of assembling the intraluminal imaging device may include positioning an outer shell around the imaging assembly such that the outer shell contacts the plurality of ultrasound transducer elements. In some embodiments, the method of assembling the intraluminal imaging device may also include inserting a filling material within a space between adjacent ultrasound transducer elements, the flexible substrate, and the outer shell. In some embodiments, positioning an outer shell may comprise positioning an acoustic matching layer around the imaging assembly. In some embodiments, positioning an outer shell may comprise positioning two or more acoustic matching layers around the imaging assembly.

In some embodiments, an imaging system is provided. The imaging system includes an intraluminal imaging device. The intraluminal imaging device includes a flexible elongate member that may be inserted into a lumen within a body of a patient. The flexible elongate member may comprise a central longitudinal axis. The intraluminal imaging device also includes an imaging assembly that may be disposed at a distal portion of the flexible elongate member. The imaging assembly may comprise a flexible substrate and a plurality of ultrasound transducer elements. The plurality of ultrasound transducer elements may be disposed on the flexible substrate. The flexible substrate may also be disposed around the central longitudinal axis of the flexible elongate member such that the ultrasound transducer elements may be oriented to face away from the central longitudinal axis and the flexible substrate. The imaging system may also include a computing device in communication with the intraluminal imaging device. The computing device may process the imaging data received from the intraluminal imaging device and may output the processed imaging data to a display.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

4

Figure 2A:
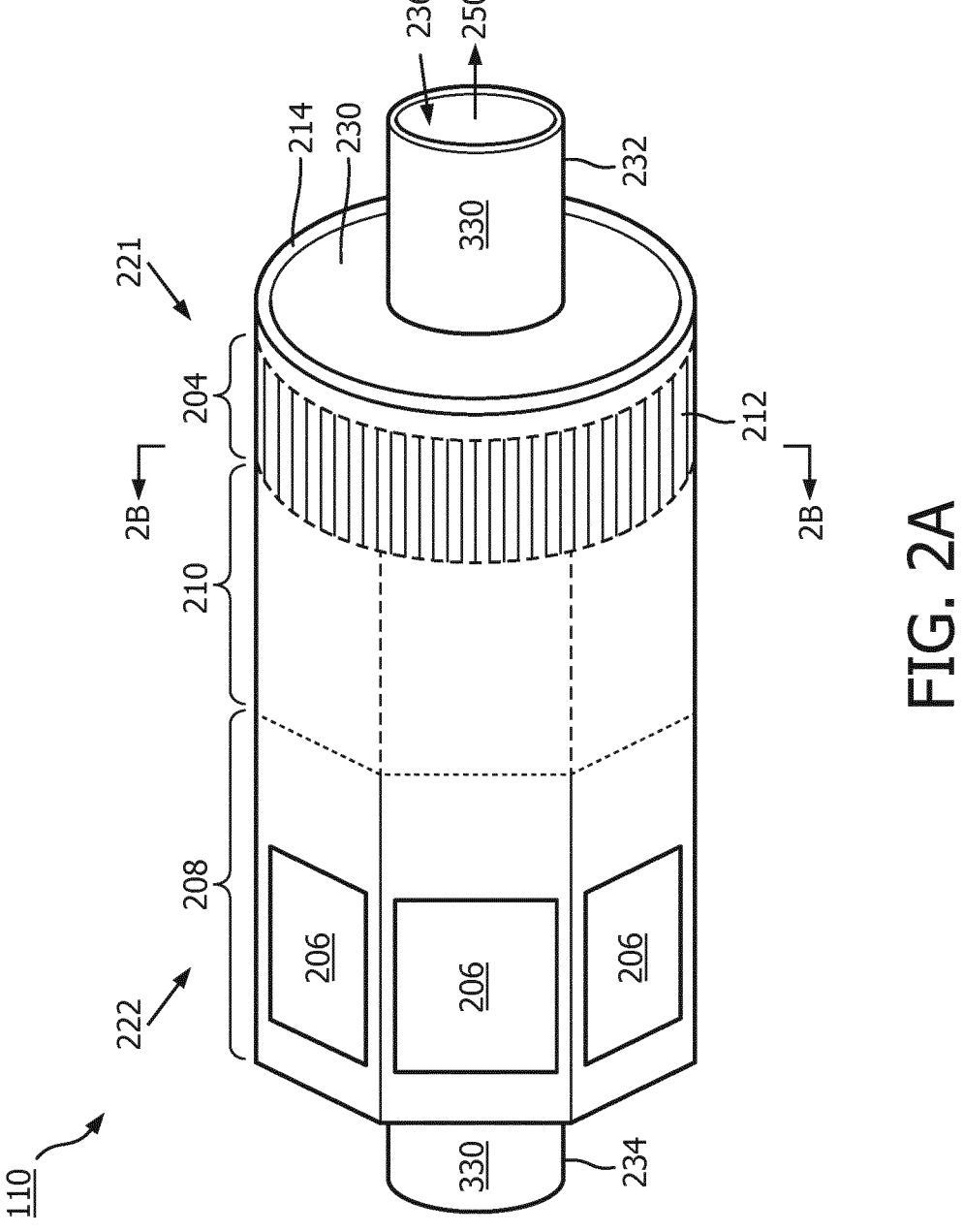
FIG. 2A is a diagrammatic side view of imaging assembly in a rolled configuration around a support member, according to aspects of the present disclosure.
Figure 3:
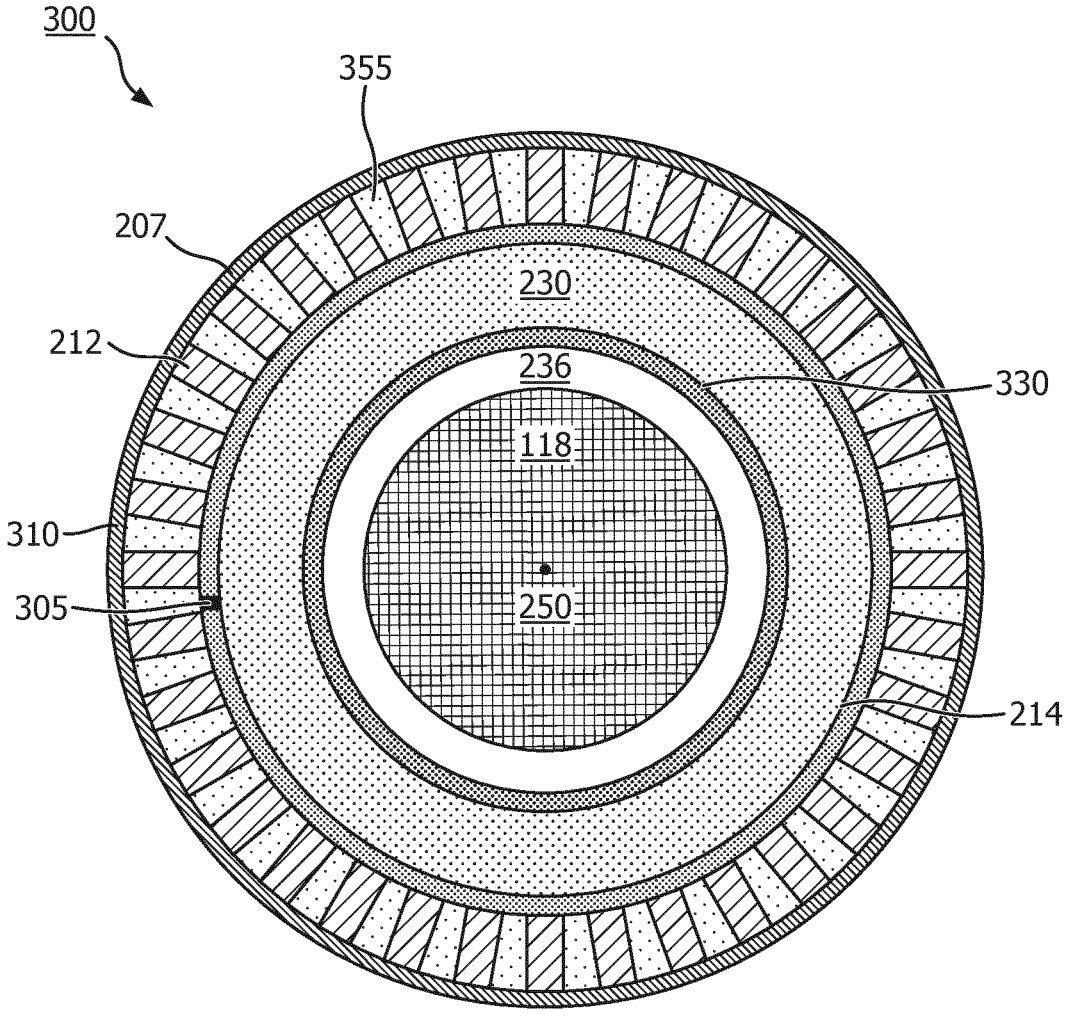

FIG. 3 is a cross-sectional view of an imaging assembly along a section 2B-2B in the rolled configuration of FIG. 2A, according to aspects of the present disclosure.

Figure 4:
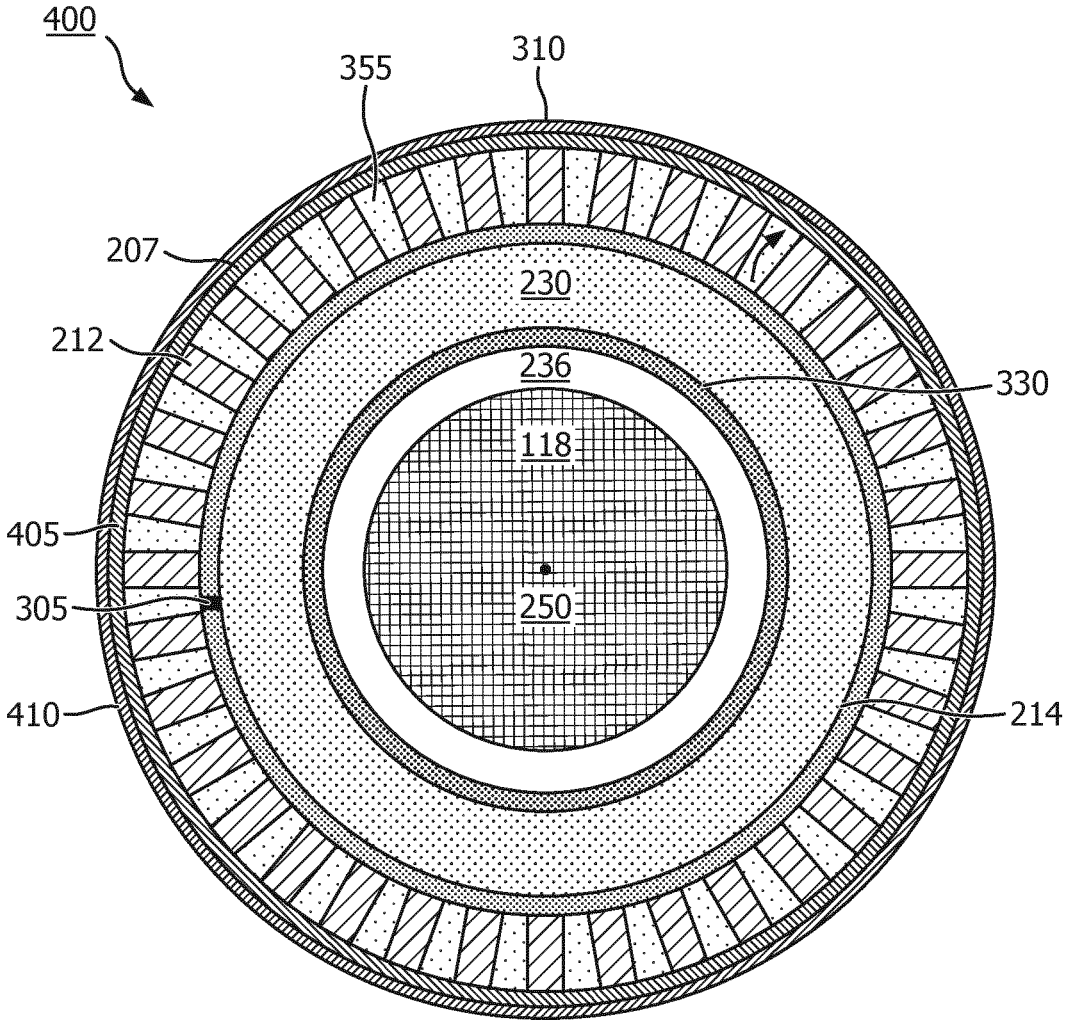

FIG. 4 is a cross-sectional view of an imaging assembly along a section 2B-2B in the rolled configuration of FIG. 2A, according to aspects of the present disclosure.

Figure 5:
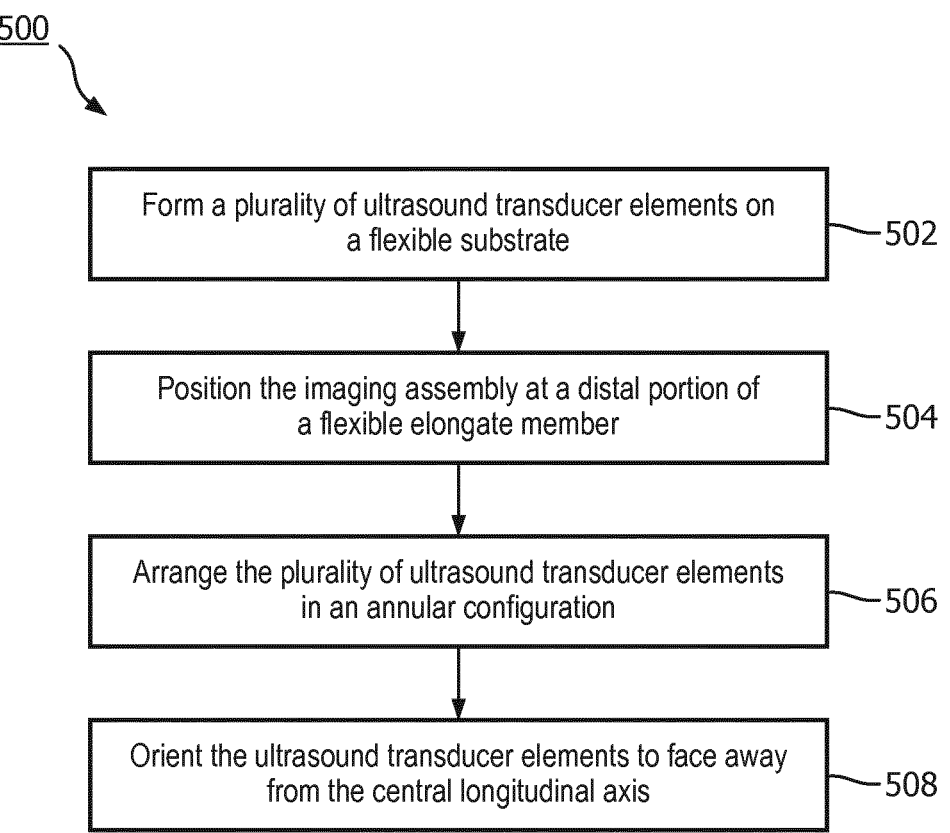

FIG. 5 is a flow diagram of a method of assembling an intraluminal imaging device, according to aspects of the present disclosure.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the imaging system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
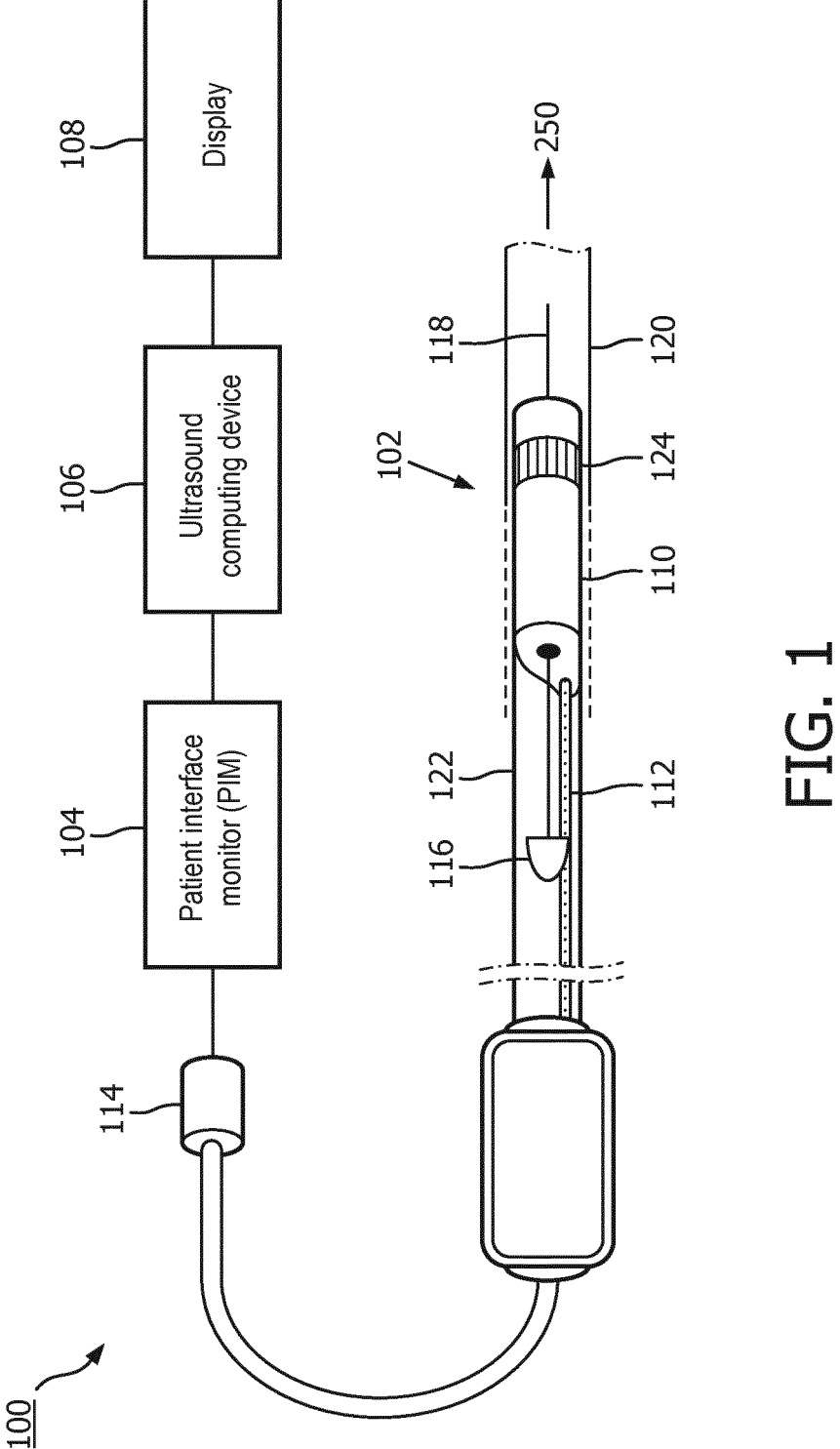
FIG. 1 is a diagrammatic schematic view of an imaging system, according to aspects of the present disclosure.

FIG. 1 is a diagrammatic schematic view of an intraluminal imaging system 100, according to aspects of the present disclosure. The intraluminal imaging system 100 may include a solid-state or phased array intraluminal ultrasound imaging device 102 such as a catheter, guide wire, or guide catheter, a patient interface module (PIM) 104, an ultrasound computing device 106, and a display 108.

The intraluminal imaging device 102 includes a flexible elongate member 122 that is configured to be inserted into a lumen, e.g., a vessel 120, within a body of a patient. The flexible elongate member 122 can include one or more elongate members that are formed of a flexible material, such as a plastic or a polymer. The flexible elongate member 122 can have generally tubular shape with a circular cross-sectional profile. In some embodiments, an inner tubular member can be concentrically positioned within an outer tubular member. The flexible elongate member 122 may include a proximal portion, a central portion, a distal portion, and a longitudinal axis 250. The longitudinal axis 250 can be a central longitudinal axis in some embodiments. A connector 114 can be disposed at the proximal portion of the flexible elongate member. The central portion extends between the proximal portion and the distal portion. A imaging device or imaging assembly 110 can be disposed at the distal portion of the flexible elongate member 122. The imaging assembly 110 includes a plurality of transducer array 124 in communication with one or more controllers. As shown in FIG. 2, for example, the imaging assembly 110 includes transducer controllers 206 in communication with transducer elements 212 of the transducer array 124.

At a high level, the ultrasound imaging assembly 110 emits ultrasonic energy from the transducer array 124 included in imaging assembly 110 and mounted near a distal end of the catheter device 102. The ultrasonic energy is reflected by tissue structures in the medium, such as a vessel 120, surrounding the imaging assembly 110, and the ultrasound echo signals are received by the transducer array 124. The PIM 104 transfers the received echo signals to the ultrasound computing device 106 where the ultrasound image is reconstructed and displayed on the display or monitor 108. The ultrasound computing device 106 or computer can include one or more processors and any suitable memory. The ultrasound computing device 106 can be operable to facilitate the features of the intraluminal imaging system 100 described herein. For example, the processor can execute computer readable instructions stored on the non-transitory tangible computer readable medium.

The PIM 104 facilitates communication of signals between the ultrasound processing system 106 and the imaging assembly 110 included in the imaging device 102. In some embodiments, the PIM 104 performs preliminary processing of the echo data prior to relaying the data to the ultrasound computing device 106. In examples of such embodiments, the PIM 104 performs amplification, filtering, and/or aggregating of the data. In some embodiments, the PIM 104 also supplies high- and low-voltage DC power to support operation of the intraluminal imaging device 102 including circuitry within the imaging assembly 110.

The ultrasound computing device or console 106 receives the echo data from the imaging assembly 110 of the intraluminal imaging device 102 by way of the PIM 104 and processes the data to reconstruct an image of the tissue structures in the medium surrounding the imaging assembly 110. The ultrasound computing device 106 outputs image data such that an image of the vessel 120, such as a cross-sectional image of the vessel 120, is displayed on the display 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or any suitable lumen inside the body. The intraluminal imaging device 102 is an intravascular imaging device or IVUS imaging device in some embodiments. The intraluminal imaging device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the intraluminal imaging device 102 may be may be used to examine man-made structures such as, but without limitation, heart valves, stents, shunts, filters and other devices.

In some embodiments, the intraluminal imaging device 102 includes some features similar to traditional solid-state intravascular imaging catheters, such as the EagleEye® catheter available from Volcano Corporation and those disclosed in U.S. Pat. No. 7,846,101 hereby incorporated by reference in its entirety. For example, the intraluminal imaging device 102 includes the imaging assembly 110 near a distal end of the imaging device 102 and a transmission line cable 112 extending along the longitudinal body of the imaging device 102. The transmission line bundle or cable 112 can include a plurality of conductors, including one, two, three, four, five, six, seven, or more conductors. The cable 112 facilitates communication of electrical signals between the imaging assembly 110 and the ultrasound computing device 106.

The transmission line cable 112 terminates in a PIM connector 114 at a proximal end of the imaging device 102. The PIM connector 114 electrically couples the transmission line cable 112 to the PIM 104 and physically couples the intraluminal imaging device 102 to the PIM 104. In some embodiments, the intraluminal imaging device 102 further includes a guide wire exit port 116. Accordingly, in some instances the intraluminal imaging device is a rapid-exchange catheter. The guide wire exit port 116 allows a guide wire 118 to be inserted towards the distal end in order to direct the imaging device 102 through the vessel 120.

The system 100, the device 102, the imaging assembly 110, and/or other components of the system 100 can include features similar to those described in U.S. application Ser. No. 14/137,269, filed Dec. 20, 2013, the entirety of which is hereby incorporated by reference.

FIG. 2A is a diagrammatic side view of imaging assembly 110 in a rolled configuration around a support member 330. In some examples, the imaging assembly 110 comprises a transducer region 204, a controller region 208, and a transition region 210. In some embodiments, the imaging assembly 110 may include a plurality of ultrasound transducer elements 212 disposed in the transducer region 204 at a distal portion 221 of the imaging assembly 110 around the support member 330 and the longitudinal axis 250 of the flexible elongate member 122. In some embodiments, the imaging assembly 110 may include a plurality of transducer controllers 206 disposed in the control region 208 at a proximal portion of the imaging assembly 110 around the longitudinal axis 250 of the flexible elongate member 122. In some embodiments, the transducer elements 212 and/or the controllers 206 can be positioned in in an annular configuration, such as a circular configuration or in a polygon configuration, around the longitudinal axis 250. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

In some examples, the transition region 210 is disposed between the transducer region 204 and the control region 208 and may provide conductive traces that extend between the transducer controllers 206 and the transducers 212. The conductive traces facilitate electrical communication between the controllers 206 and the transducers 212.

The transducer region 204 is disposed at the distal portion 221 of the imaging assembly 110. For example, the transducers 212 are mounted on a flexible substrate 214 at the distal portion 221. In some examples, the flexible substrate 214 may extend from the distal portion 221 to proximal portion 222 of the imaging assembly 110. The control region 208 is disposed at the proximal portion 222 of the flexible substrate 214. For example, the transducer controllers 206 may be mounted on the flexible substrate 214 at the proximal portion 222. The transition region 210 is disposed between the control region 208 and the transducer region 204. Dimensions of the transducer region 204, the control region 208, and the transition region 210 can vary in different embodiments.

In some embodiments, the flexible substrate 214, on which the transducer controllers 206 and the transducers 212 are mounted, may provide structural support and interconnects for electrical coupling between the transducer controllers 206 and the transducers 212. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). As shown and described herein, a distal portion of the flexible substrate 214 may be configured to be wrapped around a support member 330 (See FIGS. 2A and 3) to form a cylindrical toroid in some instances. Therefore, the thickness of the film layer of the flexible substrate 214 is generally related to the degree of curvature in the imaging assembly 110. In some embodiments, the film layer is between 5 µm and 100 µm, with some particular embodiments being between 12.7 µm and 25.1 µm.

The support member 330 can be disposed at the distal portion of the flexible elongate member along the central longitudinal axis 250. In some embodiments, the support member 330 can define a lumen 236 extending longitudinally. The lumen 236 is in communication with the guide wire exit port 116 and is sized and shaped to receive the guide wire 118 (FIG. 1). The support member can have any suitable shape. The support member 330 may be composed of a metallic material, such as stainless steel, or non-metallic material, such as a plastic or polymer. The support member 330 can include can be manufactured accordingly to any suitable process. The support member 330 can include body and one or more stands at distal and proximal portions of the support member 330. A distal stand may extend vertically/radially form the body of the support member to the flexible substrate 214 to support the flexible substrate 214 and elevate from the body of the support member 330. To improve acoustic performance, the vertical or radial space between the flexible substrate 214 and the body of the support member 330 can be filled with a backing material (e.g., backing material 230 of FIGS. 3 and 4). The backing material can attenuate the acoustic waves from the transducer elements 212 that to travel inward toward the longitudinal axis 250 so that the ultrasound echoes received from the vessel 120 are from ultrasound waves traveling outward. In some examples, the support member 330 includes a proximal flange 234 and a distal flange 232 that extend proximally and distally from the main body of the support member 330. The flanges 232, 234 and the main body of the support member 330 can define a lumen extending longitudinally through the support member 330 through which the guide wire 118 extends.

Figure 2B:
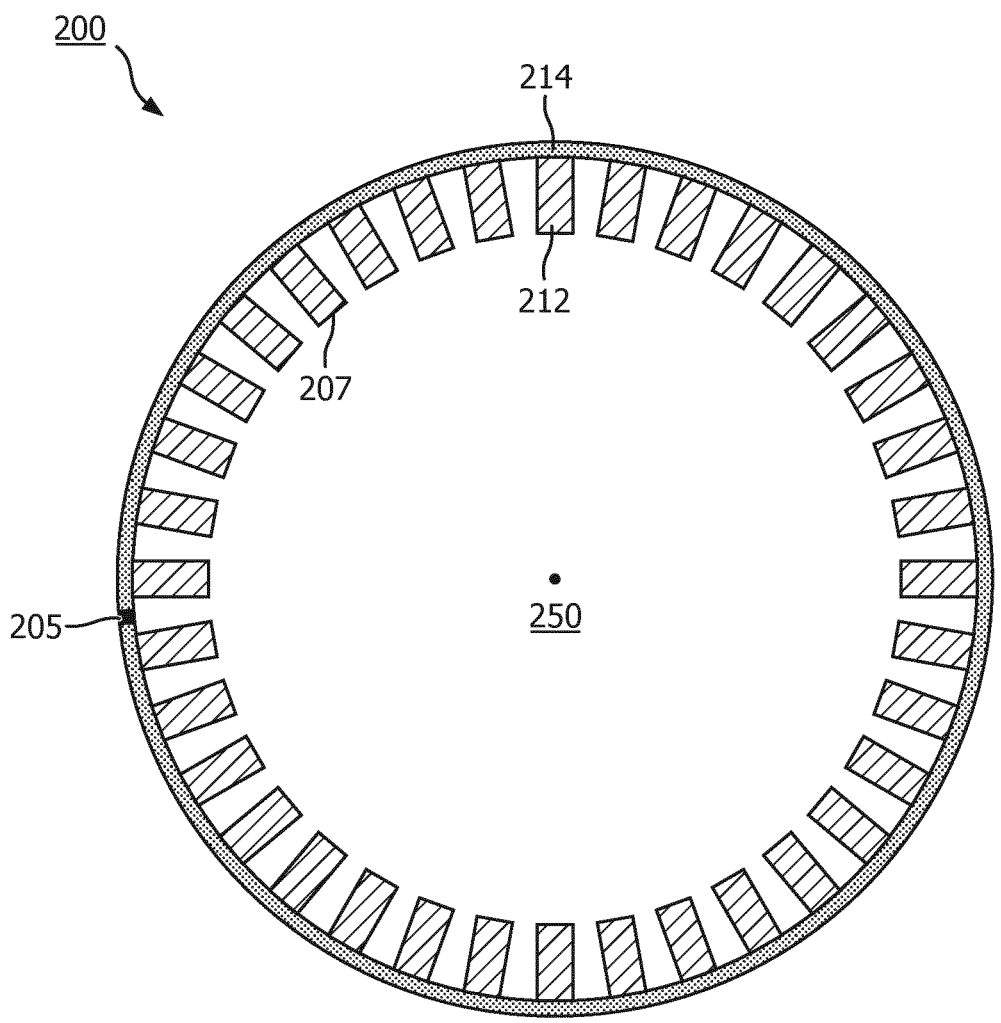
FIG. 2B is a cross-sectional view of an imaging assembly along a section 2B-2B in the rolled configuration of FIG. 2A, according to the prior art.

FIG. 2B is a cross-sectional view showing a prior art arrangement of portions of an imaging assembly along a section 2B-2B in the rolled configuration of FIG. 2A. Diagram 200 shows the flexible substrate 214 rolled around the central longitudinal axis 250 of the flexible elongate member 122. Diagram 200 also shows the ultrasound transducer elements 212 that are mounted on the flexible substrate 214. In some embodiments, the ultrasound transducer elements 212 are mounted on a flat flexible substrate 214, and the flat flexible substrate 214 is rolled around the central longitudinal axis 250 such that relative to the ultrasound transducer elements 212, the flexible substrate 214 is farther away from the central longitudinal axis 250 than the transducer elements 212. This orientation of the transducer elements 212 can be referenced as inwardly facing in that a leading edge 207 of the transducer elements 212 faces inwardly towards the central longitudinal axis 250. The leading edge 207 may be a surface of the transducer elements 212 opposite the surface that is connected to the flexible substrate 214.

The ultrasound transducer elements 212 are configured to transmit acoustic waves away from the longitudinal axis 250. The ultrasound energy may thus pass through the material of the flexible substrate 214. In existing devices, the material of the flexible substrate 214 is selected to optimize flexibility so that the substrate 214 can be rolled around the central longitudinal axis 250. The material of the flexible substrate 214 is not selected to maximize acoustic performance. Indeed, the material forming the flexible substrate 214, such as polyimide, has an acoustic impedance that that hinders transmission of ultrasound energy, which correspondingly hinders the image quality of the imaging assembly.

After rolling the flexible substrate 214 around the longitudinal axis 250, an opening may exist between the two edges of the flexible substrate 214. This opening would allow fluid ingress. Accordingly, in existing devices, an additional step during manufacturing is taken to manually add a bead of material along the edges to provide a seal 205 to connect the two edges of the rolled flexible substrate 214 to close the opening. The seal 205 prevents body fluid, such as blood from entering the imaging assembly 110.

FIG. 3 is a cross-sectional view of an imaging assembly along a section 2B-2B in the rolled configuration of FIG. 2A. Imaging assembly 300 shows the flexible substrate 214 rolled around the central longitudinal axis 250 of the flexible elongate member 122. Imaging assembly 300 also shows the ultrasound transducer elements 212 that are mounted on the flexible substrate 214. The arrangement of FIG. 3 addresses the deficiencies identified with respect to FIG. 2B, and advantageously allows more efficient manufacturing and better image quality. In some embodiments, the ultrasound transducer elements 212 are mounted on a flat flexible substrate 214, and the flat flexible substrate 214 is rolled around the central longitudinal axis 250 such that relative to the ultrasound transducer elements 212, the transducer elements 212 are farther away from the central longitudinal axis 250 than the flexible substrate 214. That is, relative to the ultrasound transducer elements 212, the flexible substrate 214 is closer to the longitudinal axis 250. This orientation of the transducer elements 212 can be referenced as outwardly facing in that the leading edge 207 of the transducer elements 212 faces outwardly away from the central longitudinal axis 250. The ultrasound transducer elements 212 are configured to transmit acoustic waves away from the longitudinal axis 250 and away from the flexible substrate 214. Because the flexible substrate 214 is closer to the central longitudinal axis 250, the material of the flexible substrate 214 no longer interrupts the transmission of ultrasound energy away from the central longitudinal axis 250.

The flexible substrate 214 and the ultrasound transducer elements 212 are surrounded by an outer shell 310. The outer shell 310 contacts at least the leading edges 207 of the transducer elements 212 such that the transducer elements are well coupled to the outer shell 310. The outer shell 310 can be flexible in some instances. In some examples, the intraluminal imaging device 102 including the imaging assembly 110 may be inserted into the body of a patient such as a blood vessel. The outer shell 310 may seal the imaging assembly 110 and prevents any body fluid including blood from entering the imaging assembly 110. In the arrangement of FIG. 3, while an opening 305 exists between edges of the flexible substrate 214, no extra step may be required to seal the opening 305 because the outer shell 310 seals the imaging assembly 110, including the opening 305. This advantageously removes a manual manufacturing step and improves manufacturing speed/efficiency.

In some embodiments, as shown in imaging assembly 300, the ultrasound transducer elements 212 are positioned in an annular/circumferential configuration around and equidistant from the longitudinal axis 250. The ultrasound transducer elements 212 may be configured to transmit acoustic waves away from the longitudinal axis 250 through the material of the outer shell 310. Thus, the outer shell 310 may be one or more acoustic matching layers selected to have optimized acoustic impedance and image quality for the imaging assembly 110. The material(s) of the outer shell 310 can have acoustic impedance(s) that allow the ultrasound energy in order to efficiently deliver ultrasound energy through blood to tissue, such as a vessel wall. The materials may broaden the spectrum associated with the ultrasound waves and allow for increased energy to be transmitted to the tissue. Exemplary materials include polyethylene, polyethylene terephalate, polyethylene terephthalate polyester, pebax, etc. The type and thickness(es) of the exemplary materials can be varied to achieve the required matching acoustic properties as defined herein. For example, the outer shell 310 can have an acoustic impedance between the acoustic impedance of the transducer elements 212 and the acoustic impendence of the body tissue into which the ultrasound energy is directed.

The arrangement described herein advantageously allows for materials that are selected to match acoustic impedances are positioned in the transmission path the ultrasound energy emitted by the transducer elements 212. In the existing devices, the type of the material and its thickness is limited to materials that can be used in the fabrication of the flexible circuit 214. For example the flexible circuit 214 is not fabricated using polyethylene because the material is too weak to withstand the stresses during flex circuit manufacturing process. This creates limitation in obtaining more optimal acoustic design. According to the arrangement described herein, polyethylene and/or other suitable materials that provide better acoustic designed are advantageously positioned around the transducer elements 212 that face outward away from the central longitudinal axis 250. Thus, the emitted ultrasound energy travels through the better acoustic materials to the tissue, rather than through the material forming the flexible substrate 214, which has poorer acoustic properties. Moreover, the best transmission of the energy from the transducer to the imaging medium uses a concept of quarter wavelength matching layer. The wavelength k equals the sound velocity in the material/frequency. Depending on the material specific sound velocity and frequency of operation, there is a very specific thickness that is optimal. Obtaining this very specific thickness when using material used in flex circuit operation is very difficult to achieve. According to the arrangement described herein, the specific thickness of the one or more layers of the outer shell 310 can be advantageously selected to maximize optimal acoustics and imaging quality.

In some examples, the ultrasound transducer elements 212 are formed on the flexible substrate 214 such that a distance between the adjacent ultrasound transducer elements 212 at the outer shell 310 is between 5 µm and 15 µm, for example. The one or more layers of the outer shell 310 can be tubing, such as heat shrink tubing. This advantageously provides continuous surface that seals the imaging assembly 110, compared to a bead of material between the edges of the flexible substrate in previous arrangements (FIG. 2B).

In some examples, a filling material 355 may be inserted between the flexible substrate 214 and the outer shell 310 such that the filling material 355 fills the space between adjacent transducers 212, the flexible substrate 214 and the outer shell 310. In some examples, the filling material 355 is an adhesive, such as an epoxy, an epoxy composite material, etc. In some instances, the filling material 355 is a material configured to attenuate sound waves. In some examples, the filling material 355 can be cured after being positioned in the interstitial spaces. In some instances, the filling material 355 also fills the opening 305 between edges of the flexible substrate 214. In some examples, the filling material 355 couples the leading edge 207 of the transducer elements 212 to the outer shell 310.

As shown in FIG. 3, the flexible substrate 214 is wrapped around a support member 330 to form a generally cylindrical or cylindrical toroid. In some examples, the space between the support member 330 and the flexible substrate 214 may be filled with an acoustic backing material 230. The backing material 230 and the material of the flexible substrate 214 may be selected to provide support as well as to attenuate acoustic waves to travel inward toward the longitudinal axis 250. In some examples, the support member 330 has a cylindrical shape and is centered around the central longitudinal axis 250. In some examples, the support member 330 may define a lumen 236 around the longitudinal axis 250. In some examples, the guide wire 118 is inserted through the lumen 236. The guide wire 118 allows for the imaging device 102 to be steered to a predetermined location within the patient body.

In some examples, as shown in imaging assembly 300, the leading edge 207 the ultrasound transducer elements 212 is farther away from the longitudinal axis 250 and in contact with, e.g., is coupled to, the outer shell 310. The opposite edge of the ultrasound transducer elements 212 closer to the longitudinal axis 250 is mounted to the flexible substrate 214. In some examples, the leading edge 207 attached to the outer shell 310. In some examples, when the imaging elements 212 are activated, sound waves are emitted in both inward and outward directions. The acoustic matching material(s) of the outer shell 310 are selected such that the propagation of the acoustic signal outward and away from the longitudinal axis 250 to the body tissue is enhanced. The flexible substrate 214 and/or the backing material 230 are selected to attenuate the inward directed acoustic waves such that the inward acoustic waves do not reach the body tissue.

In some embodiments, the ultrasound transducer elements 212 may not be radially centered around the longitudinal axis 250. In some examples, the ultrasound transducer elements 212 may not cover a complete circle as shown in FIGS. 2B, 3, and 4 and may only cover one or more sections of a circle.

FIG. 4 is a cross-sectional view of an imaging assembly along a section 2B-2B in the rolled configuration of FIG. 2A. Imaging assembly 400 includes similar components as those described with respect to the imaging assembly 300 (FIG. 3). Additionally, the outer shell 310 of imaging assembly 400 comprises of two outer shell layers 405 and 410. In some examples, the materials, thicknesses, and/or other properties of the layers 405 and 410 are selected such to improve the acoustic matching between the ultrasound transducer elements 212 and the material surrounding the intraluminal imaging device 102. In some examples, the outer shell 310 comprises of three or more outer shell layers such that by changing the acoustic properties of the outer shell layers, the acoustic matching can be optimized. Improved acoustic matching corresponds to improved image quality.

In some examples, during manufacturing, a first, inner layer 405 is deposited/laminated on the ultrasound transducer elements 212 prior to the transducer elements being diced. Then the dicing of the transducer elements 212 and the acoustic matching layer 405 is performed together. In some examples, the second, outer layer 410 is heat shrinkable and is positioned around the first layer 405 and transducer elements 212. The outer layer 410 can be shrunk around the first layer 405 and the transducer elements 212 using heat.

As shown in FIGS. 3 and 4, in some embodiments, the outer layer 310 may perform the function of a matching layer between the ultrasound transducer elements 212 and the medium being imaged and a thickness of the outer layer 310 may be selected such that the outer layer 310 may perform as a quarter wavelength matching layer to enhance the transmission of energy from the transducer elements 212 to the medium being imaged. In some examples, the flexible substrate 214 may not need to provide transmission of energy and it may be selected of a material such that the flexible substrate 214, alone or in combination with the backing material 230, hinder the transmission of ultrasound energy inward and toward the central longitudinal axis 250. In some examples, the outer layer 310 includes two or more layers of different material.

FIG. 5 is a flow diagram of a method 500 of assembling an intraluminal imaging device, including an imaging assembly is described herein. It is understood that the steps of method 500 may be performed in a different order than shown in FIG. 5, additional steps can be provided before, during, and after the steps, and/or some of the steps described can be replaced or eliminated in other embodiments. The steps of the method 500 can be carried out by a manufacturer of the intraluminal imaging device 102.

At step 502, the method 500 includes forming a plurality of ultrasound transducer elements on a flexible substrate to form an imaging assembly. For example, the ultrasound transducer elements 212 are disposed on the flexible substrate 214 to create the imaging assembly 110. At step 504, the method 500 includes positioning the imaging assembly at a distal portion of a flexible elongate member. For example, the imaging assembly 110 may be disposed at a distal portion of the flexible elongate member 122 such that imaging assembly 110 can be used to image the lumen when the distal portion of the flexible elongate member 122 is inserted into the patient body.

At step 506, the method 500 includes arranging the plurality of ultrasound transducer elements around the central longitudinal axis of the flexible elongate member. For example, the plurality of ultrasound transducer elements 212 may be arranged in an annular configuration, such as in a circular configuration or a polygon configuration. As shown in FIGS. 2A, 3 and 4, for example, the ultrasound transducers 212 are disposed around the longitudinal axis 250 of the flexible elongate member 122. Also, as shown in FIGS. 3 and 4, the ultrasound transducers 212 may be mounted to the flexible substrate 214.

At step 508, the method 500 includes orienting the ultrasound transducer elements to face away from the central longitudinal axis. For example, a leading edge of the transducer elements can face away from the central longitudinal axis. In some embodiments, the acoustic waves from the transducer elements are transmitted outward away from the central longitudinal axis 250 and also away from the flexible substrate 214.

In some embodiments, the method 500 includes positioning the flexible substrate around a support member. For example, the flexible substrate 214 may be wrapped in a rolled or cylindrical configuration around the support member 330 of FIGS. 3 and 4. In some embodiments the method 500 includes inserting a backing material between the flexible substrate and the support member. The backing material can be configured to attenuate sound waves that are directed inwardly toward the central longitudinal axis of the flexible elongate member. By attenuating these sound waves, acoustic energy is directed from the transducer elements outwardly from the central longitudinal axis to the physiology within the patient body. In some embodiments, the method 500 includes arranging the support member along the central longitudinal axis of the flexible elongate member. In some embodiments, the method 500 includes extending a guide wire along the central longitudinal axis of the flexible elongate member within a lumen defined by the support member.

In some embodiments, the method 500 includes positioning an outer shell around the imaging assembly such that the outer shell contacts the plurality of ultrasound transducer elements. As noted above with respect to FIGS. 3 and 4, for example, one edge of the ultrasound transducers 212 are coupled between the flexible substrate 214 and the opposite leading can be coupled to the outer shell 310. Positioning an outer shell around the imaging assembly can include positioning one, two, or more acoustic matching layers around imaging assembly. In some embodiments, the method 500 includes inserting a filling material within a space between adjacent ultrasound transducer elements, the flexible substrate, and the outer shell.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
   a flexible elongate member configured to be inserted into a body lumen within a patient, the flexible elongate member comprising a central longitudinal axis;
   an imaging assembly disposed at a distal portion of the flexible elongate member, the imaging assembly comprising:
   a flexible substrate rolled around the central longitudinal axis such that a first end and a second end of the flexible substrate are spaced from one another such that an unsealed gap is formed between the first end and the second end, wherein the gap extends between an outer surface and an inner surface of the flexible substrate;
   a plurality of ultrasound transducer elements disposed on the flexible substrate; and an outer shell positioned around the flexible substrate and the plurality of ultrasound transducer elements such that the outer shell is radially spaced from the gap to seal the imaging assembly from fluid ingress.

2. The intraluminal imaging device of claim 1, wherein the imaging assembly further comprises:

a support member, wherein the flexible substrate is positioned around the support member.

3. The intraluminal imaging device of claim 2, wherein the imaging assembly further comprises:

a backing material disposed between the flexible substrate and the support member.

4. The intraluminal imaging device of claim 2, wherein the support member is disposed longitudinally along the central longitudinal axis of the flexible elongate member.

5. The intraluminal imaging device of claim 2, wherein the support member defines a lumen configured to accommodate a guide wire extending along the central longitudinal axis.

6. The intraluminal imaging device of claim 1, wherein the plurality of ultrasound transducer elements contact the outer shell.

7. The intraluminal imaging device of claim 6, wherein the imaging assembly further comprises:

a filling material positioned in a space between adjacent ultrasound transducer elements of the plurality of ultrasound transducer elements, the flexible substrate, and the outer shell.

8. The intraluminal imaging device of claim 6, wherein the outer shell comprises an acoustic matching layer.

9. The intraluminal imaging device of claim 6, wherein the outer shell comprises of two or more acoustic matching layers.

10. The intraluminal imaging device of claim 1, wherein the flexible substrate is closer to the central longitudinal axis than the plurality of ultrasound transducer elements.

11. The intraluminal imaging device of claim 1, wherein the ultrasound transducer elements are oriented to face away from the central longitudinal axis and the flexible substrate.

12. A method of assembling an intraluminal imaging device, comprising:

obtaining an imaging assembly comprising:

a flexible substrate; and a plurality of ultrasound transducer elements disposed on the flexible substrate;

rolling the flexible substrate in a cylindrical configuration around a central longitudinal axis at a distal portion of a flexible elongate member configured to be inserted into a body lumen within a patient such that a first end and a second end of the flexible substrate are spaced from one another to form an unsealed gap is formed between the first end and the second end, wherein the gap extends between an outer surface and an inner surface of the flexible substrate; and positioning an outer shell around the flexible substrate such that the outer shell is radially spaced from the gap to seal the imaging assembly from fluid ingress.

13. The method of claim 12, further comprising:

positioning the flexible substrate around a support member.

14. The method of claim 13, further comprising:

inserting a backing material between the flexible substrate and the support member.

15. The method of claim 13, further comprising:

arranging the support member along the central longitudinal axis of the flexible elongate member, wherein the support member has a cylindrical shape.

16. The method of claim 13, further comprising:

extending a guide wire along the central longitudinal axis of the flexible elongate member within a lumen defined by the support member.

17. The method of claim 12, wherein the outer shell contacts the plurality of ultrasound transducer elements.

18. The method of claim 17, further comprising:

inserting a filling material within a space between adjacent ultrasound transducer elements of the plurality of ultrasound transducer elements, the flexible substrate, and the outer shell.

19. The method of claim 17, wherein the positioning an outer shell comprises:

positioning an acoustic matching layer around the imaging assembly.

20. The method of claim 17, wherein the positioning an outer shell comprises:

positioning two or more acoustic matching layers around the imaging assembly.

21. An imaging system, comprising:

an intraluminal imaging device, comprising:

a flexible elongate member configured to be inserted into a body lumen within a patient, the flexible elongate member comprising a central longitudinal axis;

an imaging assembly disposed at a distal portion of the flexible elongate member, the imaging assembly comprising:

a flexible substrate rolled around the central longitudinal axis such that a first end and a second end of the flexible substrate are spaced from one another such that an unsealed gap is formed between the first end and the second end, wherein the gap extends between an outer surface and an inner surface of the flexible substrate;

a plurality of ultrasound transducer elements disposed on the flexible substrate; and an outer shell positioned around the flexible substrate and the plurality of ultrasound transducers such that the outer shell is radially spaced from the gap to seal the imaging assembly from fluid ingress; and a computing device in communication with the intraluminal imaging device, wherein the computing device is configured to process imaging data received from the intraluminal imaging device and to output the processed imaging data to a display.

* * * * *